United States Patent
Eshoo et al.

(10) Patent No.: US 9,109,222 B2
(45) Date of Patent: Aug. 18, 2015

(54) NUCLEIC ACID SAMPLE PREPARATION METHODS AND COMPOSITIONS

(75) Inventors: Mark Eshoo, Solana Beach, CA (US); John Picuri, Carlsbad, CA (US); Stanley Motley, Carlsbad, CA (US)

(73) Assignee: IBIS BIOSCIENCES, INC., Carlsbad, CA (US)

( * ) Notice: Subject to any disclaimer, the term of this patent is extended or adjusted under 35 U.S.C. 154(b) by 0 days.

(21) Appl. No.: 13/337,828

(22) Filed: Dec. 27, 2011

(65) Prior Publication Data

US 2012/0172258 A1 Jul. 5, 2012

Related U.S. Application Data

(60) Provisional application No. 61/427,321, filed on Dec. 27, 2010.

(51) Int. Cl.
*C40B 50/06* (2006.01)
*C12N 9/12* (2006.01)
*C09K 3/00* (2006.01)
*C12N 15/10* (2006.01)
*C12Q 1/68* (2006.01)

(52) U.S. Cl.
CPC ............ *C12N 15/10* (2013.01); *C12N 15/1093* (2013.01); *C12Q 1/686* (2013.01)

(58) Field of Classification Search
CPC .................................. C40B 50/06; C12N 9/12
USPC ......................................................... 506/26
See application file for complete search history.

(56) References Cited

U.S. PATENT DOCUMENTS

| 2002/0119465 A1 * | 8/2002 | Zhao et al. ............. 435/6 |
| 2006/0246462 A1 | 11/2006 | Hogrefe et al. |
| 2007/0031857 A1 * | 2/2007 | Makarov et al. ......... 435/6 |
| 2010/0021973 A1 | 1/2010 | Makarov et al. |
| 2010/0105052 A1 * | 4/2010 | Drmanac et al. ......... 435/6 |

FOREIGN PATENT DOCUMENTS

WO 2011047307 A1 4/2011

OTHER PUBLICATIONS

Zhang et al., PCR microfluidic devices for DNA amplification, Biotechnology Advances 24 (2006) 243-284.*
Nunez et al., Application of circular ligase to provide template for rolling circle amplification of low amounts of fragmented DNA, Nineteenth International Symposium on Human Identification, Madison, WI, Oct. 2, 2008, Hosted by Promega pp. 1-7.*
Chelliserrykattil et al., Polymerase amplification, cloning and gene expression of benzo-homologous "yDNA" base pairs, ChemBioCHem 2008, 9, 2976-2980.*
Li et al.,Primase-based whole genome amplification, Nucleic Acid Research Aug. 2008; 36(13):e79.*
Rodrigue et al., Whole genome amplification and de novo assembly of single bacterial cells, PlosONE Sep. 2009, vol. 4 Issue 9 e6864.*
Thorne et al., In vitro amplification or PrP sc derived from the brain and blood of sheep infected with scrapie, J Gen Virol Dec. 2008, Journal of Gen Virology Dec. 2008 vol. 89 No. 12 3177-3184.*
Pan et al., A procedure for highly specific, sensitive, and unbiased whole-genome amplification, PNAS Oct. 7, 2008 vol. 105 No. 40 15499-15504.*
ThermoScientific phi29 DNA Polymerase Product Information Sheet.*
Kwon et. al., Improved efficacy of whole genome amplification from bacterial cells, Biotechniques 37:40-44, Jul. 2004.*
International Search Report and Written Opinion for Application No. PCT/US2011/067374, mailed on Apr. 27, 2012, 11 pages.
Suppplementary European Search Report for Application No. EP11853018, mailed on Sep. 22, 2014, 3 pages.
Voelkerding K.V., et al., "Next-Generation Sequencing: from Basic Research to Diagnostics," Clinical Chemistry, 2009, vol. 55 (4), pp. 641-658.

* cited by examiner

*Primary Examiner* — Maria Leavitt
*Assistant Examiner* — Amy M Bunker
(74) *Attorney, Agent, or Firm* — David A. Casimir; Casimir Jones, S.C.

(57) ABSTRACT

The present invention provides compositions and methods for preparing a nucleic acid library in a multi-purpose buffer (e.g., employing whole genome amplification), where nucleic acid purification is not required between or during steps. In certain embodiments, small amounts of starting nucleic acid (e.g., genomic DNA) are employed and the steps are accomplished in a single container. In some embodiments, the nucleic acid library is subjected to sequencing methodologies or rolling circle amplification.

13 Claims, 10 Drawing Sheets

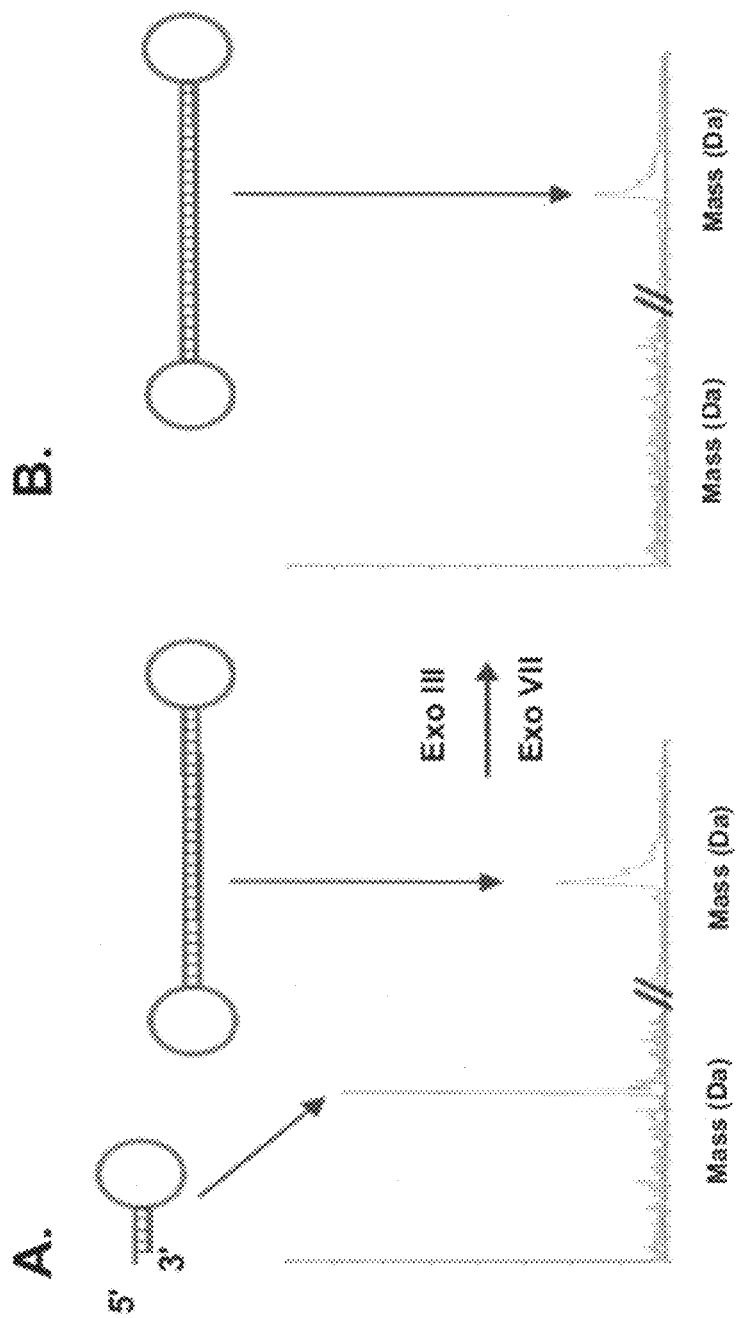

NUCLEIC ACID SAMPLE PREPARATION METHODS AND COMPOSITIONS

The present Application claims priority to U.S. Provisional Application Ser. No. 61/427,321 filed Dec. 27, 2010, the entirety of which is incorporated by reference herein.

STATEMENT REGARDING FEDERALLY SPONSORED RESEARCH OR DEVELOPMENT

This invention was made with government support under HDTRA1-10-C-0080 awarded by DTRA. The government has certain rights in the invention.

FIELD OF THE INVENTION

The present invention provides compositions and methods for preparing a nucleic acid library in a multi-purpose buffer (e.g., employing whole genome amplification), where nucleic acid purification is not required between or during steps. In certain embodiments, small amounts of starting nucleic acid (e.g., genomic DNA) are employed and the steps are accomplished in a single container. In some embodiments, the nucleic acid library is subjected to sequencing methodologies or rolling circle amplification.

BACKGROUND

In many fields of research such as genetic diagnosis, cancer research or forensic medicine, the scarcity of genomic DNA can be a severely limiting factor on the type and quantity of genetic tests that can be performed on a sample. One approach designed to overcome this problem is whole genome amplification. The objective is to amplify a limited DNA sample in a non-specific manner in order to generate a new sample that is indistinguishable from the original but with a higher DNA concentration. The aim of a typical whole genome amplification technique is to amplify a sample up to a microgram level while respecting the original sequence representation.

The first whole genome amplification methods were described in 1992, and were based on the principles of the polymerase chain reaction. Zhang and coworkers (Zhang, L., et al. Proc. Natl. Acad. Sci. USA, 1992, 89: 5847-5851; herein incorporated by reference) developed the primer extension PCR technique (PEP) and Telenius and collaborators (Telenius et al., Genomics. 1992, 13(3):718-25; herein incorporated by reference) designed the degenerate oligonucleotide-primed PCR method (DOP-PCR).

PEP involves a high number of PCR cycles, generally using Taq polymerase and 15 base random primers that anneal at a low stringency temperature. Although the PEP protocol has been improved in different ways, it still results in incomplete genome coverage, failing to amplify certain sequences such as repeats. Failure to prime and amplify regions containing repeats may lead to incomplete representation of a whole genome because consistent primer coverage across the length of the genome provides for optimal representation of the genome. This method also has limited efficiency on very small samples (such as single cells). Moreover, the use of Taq polymerase implies that the maximal product length is about 3 kb.

DOP-PCR is a method which generally uses Taq polymerase and semi-degenerate oligonucleotides (such as CGACTCGAGNNNNNNATGTGG (SEQ ID NO: 12), for example, where N=A, T, C or G) that bind at a low annealing temperature at approximately one million sites within the human genome. The first cycles are followed by a large number of cycles with a higher annealing temperature, allowing only for the amplification of the fragments that were tagged in the first step. This leads to incomplete representation of a whole genome. DOP-PCR generates, like PEP, fragments that are in average 400-500 bp, with a maximum size of 3 kb, although fragments up to 10 kb have been reported. On the other hand, as noted for PEP, a low input of genomic DNA (less than 1 ng) decreases the fidelity and the genome coverage (Kittler et al., Anal. Biochem. 2002, 300(2), 237-44).

Multiple displacement amplification (MDA, also known as strand displacement amplification; SDA) is a non-PCR-based isothermal method based on the annealing of random hexamers to denatured DNA, followed by strand-displacement synthesis at constant temperature (Blanco et al., 1989, J. Biol. Chem. 264:8935-40, herein incorporated by reference). It has been applied to small genomic DNA samples, leading to the synthesis of high molecular weight DNA with limited sequence representation bias (Lizardi et al., Nature Genetics 1998, 19, 225-232; Dean et al., Proc. Natl. Acad. Sci. U.S.A. 2002, 99, 5261-5266; both of which are herein incorporated by reference). As DNA is synthesized by strand displacement, a gradually increasing number of priming events occur, forming a network of hyper-branched DNA structures. The reaction can be catalyzed by the Phi29 DNA polymerase or by the large fragment of the Bst DNA polymerase. The Phi29 DNA polymerase possesses a proofreading activity resulting in error rates 100 times lower than the Taq polymerase.

What is needed are whole genome amplification methods that do not require nucleic acid purification between or during steps, and/or that can be accomplished in a single container.

SUMMARY OF THE INVENTION

The present invention provides compositions and methods for preparing a nucleic acid library (e.g., a DNA library) in a multi-purpose buffer (e.g., employing whole genome amplification, such as MDA), where nucleic acid purification is not required between or during steps. In certain embodiments, small amounts of starting nucleic acid (e.g., genomic DNA) are employed (e.g., picograms or nanograms) and the steps are accomplished in a single container. In some embodiments, the nucleic acid library is subjected to sequencing methodologies or rolling circle amplification.

In some embodiments, the present invention provides methods of preparing a nucleic acid library in a multi-purpose buffer, comprising: a) adding a nucleic acid sample (e.g., genomic DNA) to a multi-purpose buffer, wherein the multi-purpose buffer comprises dNTPs and primers; b) contacting the multi-purpose buffer with a plurality of substantially purified enzymes, wherein the enzymes have polymerase activity, kinase activity, and phosphatase activity, and wherein the contacting is under conditions such that amplified nucleic acid is generated; c) treating the multi-purpose buffer (e.g., by mechanical, chemical, or enzymatic methods) such that sheared amplified nucleic acid is generated; d) treating the multi-purpose buffer to inactivate the polymerase activity; and e) contacting the multi-purpose buffer with a ligase and nucleic acid adapters under conditions such that an adapter-linked nucleic acid library is generated; wherein the above steps are completed in the multi-purpose buffer without nucleic acid purification between or during some or all of the steps.

In particular embodiments, the amplified nucleic acid is generated by whole genome amplification (e.g., MDA). In further embodiments, some or all of the steps (e.g., steps a)-e)) are conducted in a single container. In other embodiments, the methods further comprise treating the multi-purpose buffer containing the adapter-linked nucleic acid library such that proteins and dNTPs are removed from the multi-purpose buffer. In particular embodiments, the treating comprises contacting the multi-purpose buffer with a proteinase and phosphatase, or column purifying the multi-purpose buffer. In other embodiments, the adapters comprise hairpin primers, and wherein the adapter-linked nucleic library comprises circular templates.

In further embodiments, the methods further comprise treating the multi-purpose buffer containing the circular templates with at least one exonuclease enzyme capable of digesting any non-circularized nucleic acid present. In some embodiments, the methods further comprise heating the multi-purpose buffer containing the exonuclease enzyme such that the exonuclease is inactivated. In additional embodiments, the adapters comprise 3' and/or 5' blocking groups, and wherein the adapter-linked library comprises end-blocked templates. In other embodiments, the methods further comprise treating the multi-purpose buffer containing the end-blocked templates with at least one exonuclease enzyme capable of digesting any non-end-blocked nucleic acid present. In additional embodiments, the methods further comprise heating the multi-purpose buffer containing the exonuclease enzyme such that the exonuclease is inactivated.

In some embodiments, the multi-purpose buffer further comprises an emulsifier. In certain embodiments, the emulsifier is a polysorbate (e.g., Tween 20, Tween 40, Tween 60, or Tween 80). In other embodiments, the multi-purpose buffer further comprises tris(hydroxymethyl)aminomethane (TRIS). In further embodiments, the multi-purpose buffer further comprises a divalent metal cation. In additional embodiments, the multi-purpose buffer further comprises an inorganic salt. In additional embodiments, the inorganic salt is ammonium sulfate.

In additional embodiments, the multi-purpose buffer further comprises polyadenylic acid. In other embodiments, the multi-purpose buffer further comprises an alpha-linked disaccharide. In some embodiments, the alpha-linked disaccharide comprises Trehalose. In further embodiments, the multi-purpose buffer further comprises a reducing agent. In particular embodiments, the reducing agent further comprises dithiothreitol (DTT). In certain embodiments, the multi-purpose buffer further comprises albumin or an albumin-like protein.

In some embodiments, the methods further comprise, after step c), incubating the multi-purpose buffer such that phosphorylated blunt ends (and/or A-tailed ends) are generated in the sheared amplified nucleic acid. In other embodiments, the genomic DNA is an amount that is between 10 pg and 50 ng (e.g., 10 pg to 50 pg, 50 pg to 1 ng, or 1 ng to 50 ng). In some embodiments, the adapter-linked nucleic acid library is subjected to a sequencing methodology or to rolling circle amplification. In certain embodiments, the plurality of substantially purified enzymes comprises phi 29 polymerase, Klenow exo-polymerase, polynucleotide kinase, a pyrophosphatase enzyme, or any combination thereof.

In some embodiments, the present invention provides compositions comprising at least four (or at least five, or at least six, or at least seven or at least eight) of the following: a) a buffering agent, b) an emulsifier, c) a divalent metal cation, d) an inorganic salt, e) polyadenylic acid, f) an alpha-linked disaccharide, g) a reducing agent, and h) albumin or an albumin-like protein.

In certain embodiments, the compositions further comprise tris(hydroxymethyl)aminomethane (TRIS). In other embodiments, the emulsifier is a polysorbate. In some embodiments, the polysorbate is selected from the group consisting of: Tween 20, Tween 40, Tween 60, or Tween 80. In further embodiments, the inorganic salt is ammonium sulfate. In additional embodiments, the alpha-linked disaccharide comprises Trehalose. In some embodiments, the reducing agent comprises dithiothreitol (DTT).

In further embodiments, the compositions further comprise dNTPs and/or primers. In other embodiments, the compositions further comprise a plurality of substantially purified enzymes, wherein the enzymes have polymerase activity, kinase activity, and phosphatase activity. In some embodiments, the plurality of substantially purified enzymes comprises a Phi 29 polymerase, Klenow exo-polymerase, a polynucleotide kinase, a pyrophosphatase, a ligase, or any combination thereof.

In some embodiments, the compositions further comprise nucleic acid adapters. In certain embodiments, the adapters comprise hairpin primers. In other embodiments, the compositions further comprise an exonuclease. In certain embodiments, the exonuclease is Exonuclease III or Exonuclease VII. In additional embodiments, the compositions further comprise random primers. In other embodiments, the random primers are suitable for use in whole genome amplification methods, such as MDA.

DESCRIPTION OF THE FIGURES

FIG. 2A shows total yield of amplified product as measured by qPCR, and FIG. 2B shows a gel electrophoresis analysis of amplified product.

FIG. 6 shows analysis of the sample with the oligos before (FIG. 6A) and after (FIG. 6B) addition of polynucleotide kinase.

FIG. 10 shows results from Example 1 and shows the ability to exonuclease digest DNA using exonuclease III and exonuclease VII in WGA buffer using DNA oligos and mass spectrometry analysis. This treated sample (FIG. 10B) and a ligation reaction not treated with the exonucleases (FIG. 10B) were then run on an ESI-TOF mass spectrometer using the T5000 system.

DETAILED DESCRIPTION

Figure 1:
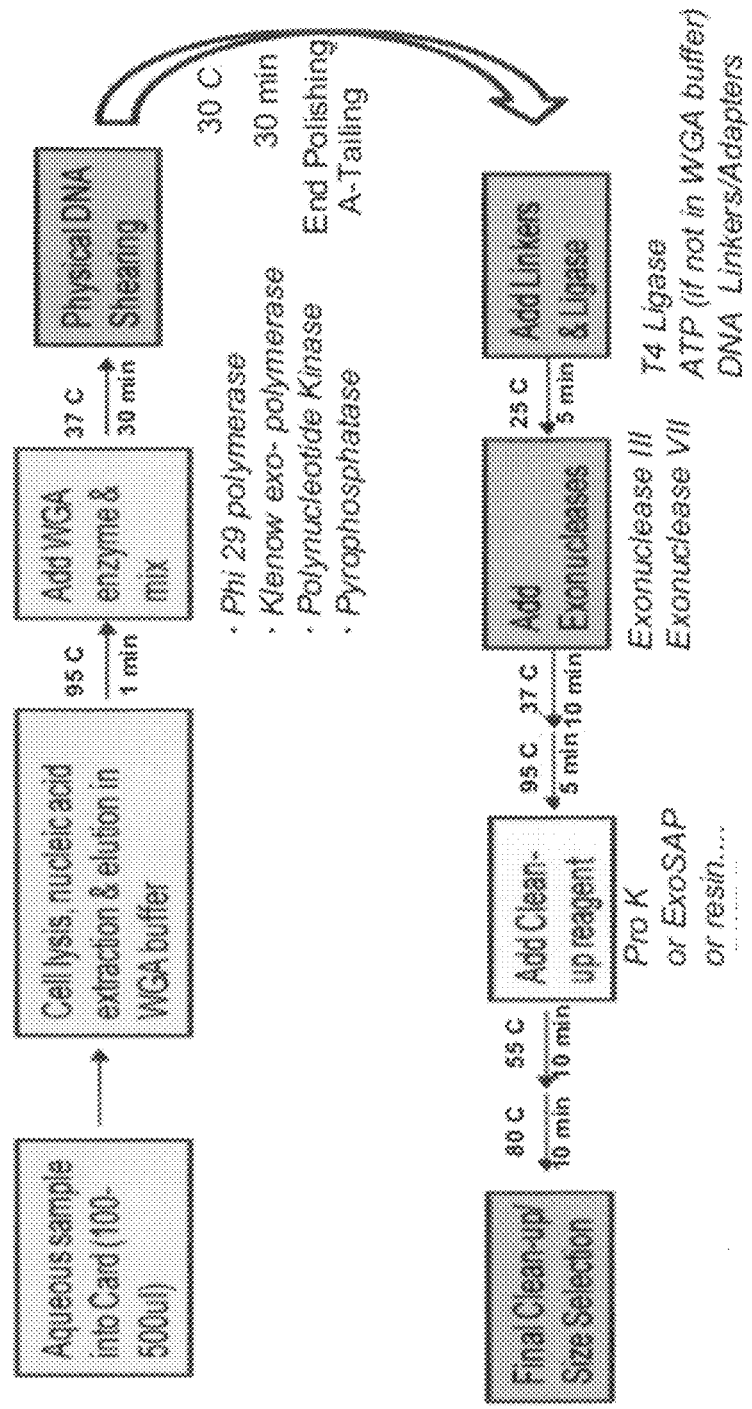
FIG. 1 shows an exemplary embodiment of a single tube library prep process in flowchart form. Specific details listed (enzymes/incubation temps & times, etc.) are merely exemplary and may vary for different types of libraries prepared.

The present invention provides compositions and methods for preparing a nucleic acid library in a multi-purpose buffer (e.g., employing whole genome amplification), where nucleic acid purification is not required between or during steps. In certain embodiments, small amounts of starting nucleic acid (e.g., genomic DNA) are employed and the steps are accomplished in a single container. In some embodiments, the nucleic acid library is subjected to sequencing methodologies or rolling circle amplification.

Current methods of preparing DNA libraries generally use a physical method for shearing of the DNA such as sonication, nebulization, etc. This is followed by a selection of fragments of the appropriate length and then enzymatic steps (including ligation of DNA adapters) to prepare the sample for sequencing. These methods require large amounts of starting material (e.g., ugs), significant amounts of time (many hours) and purification of the DNA between each step. The use of a process which does not need purification between each of the individual steps and which contains a whole genome amplification step would allow for a simpler one tube process. This in turn would allow for the creation of DNA libraries from significantly smaller amounts of starting template with a greatly reduced amount of time and effort. Such methods are provided by the present invention. The present invention provides rapid and simple methods which require no purification between steps, which can be conducted in a single tube/container, for the creation of DNA libraries from small amounts of starting DNA template for use in DNA sequencing or other applications.

In certain embodiments, the present invention uses whole genome amplification (using enzymes such as phi 29 and klenow exo-polymerases), a physical DNA fragmentation method (such as sonication), an end repair/a-tailing reaction (using enzymes such as phi 29 polymerase, klenow exo-polymerase and poly-nucleotide kinase), a ligation reaction with DNA adapters (using enzymes such as T4 ligase) and an exonuclease treatment (using enzymes such as exonuclease III and exonuclease VII) to create a library of DNA templates. In certain embodiments, the present invention requires less time (e.g., 30 minutes to 1 hour), less starting material and less manipulation/hands on time to create DNA libraries. In particular embodiments, the methods of the present invention are integrated into an automated microfluidic/Robotic system.

In some embodiments, the resulting DNA libraries are subjected to sequencing technologies. Appropriate adapters, based on the sequencing method, are employed to created the DNA library. Exemplary sequencing technologies are described below.

Illustrative non-limiting examples of nucleic acid sequencing techniques include, but are not limited to, chain terminator (Sanger) sequencing and dye terminator sequencing, as well as "next generation" sequencing techniques. Those of ordinary skill in the art will recognize that because RNA is less stable in the cell and more prone to nuclease attack experimentally RNA is usually reverse transcribed to DNA before sequencing.

Chain terminator sequencing uses sequence-specific termination of a DNA synthesis reaction using modified nucleotide substrates. Extension is initiated at a specific site on the template DNA by using a short radioactive, or other labeled, oligonucleotide primer complementary to the template at that region. The oligonucleotide primer is extended using a DNA polymerase, standard four deoxynucleotide bases, and a low concentration of one chain terminating nucleotide, most commonly a di-deoxynucleotide. This reaction is repeated in four separate tubes with each of the bases taking turns as the di-deoxynucleotide. Limited incorporation of the chain terminating nucleotide by the DNA polymerase results in a series of related DNA fragments that are terminated only at positions where that particular di-deoxynucleotide is used. For each reaction tube, the fragments are size-separated by electrophoresis in a slab polyacrylamide gel or a capillary tube filled with a viscous polymer. The sequence is determined by reading which lane produces a visualized mark from the labeled primer as you scan from the top of the gel to the bottom.

Dye terminator sequencing alternatively labels the terminators. Complete sequencing can be performed in a single reaction by labeling each of the di-deoxynucleotide chain-terminators with a separate fluorescent dye, which fluoresces at a different wavelength.

A set of methods referred to as "next-generation sequencing" techniques have emerged as alternatives to Sanger and dye-terminator sequencing methods (Voelkerding et al., *Clinical Chem.*, 55: 641-658, 2009; MacLean et al., *Nature Rev. Microbiol.*, 7: 287-296; each herein incorporated by reference in their entirety). Next-generation sequencing (NGS) methods share the common feature of massively parallel, high-throughput strategies, with the goal of lower costs in comparison to older sequencing methods. NGS methods can be broadly divided into those that require template amplification and those that do not. Amplification-requiring methods include pyrosequencing commercialized by Roche as the 454 technology platforms (e.g., GS 20 and GS FLX), the Solexa platform commercialized by Illumina, and the Supported Oligonucleotide Ligation and Detection (SOLiD) platform commercialized by Applied Biosystems. Non-amplification approaches, also known as single-molecule sequencing, are exemplified by the HeliScope platform commercialized by Helicos BioSciences, and emerging platforms commercialized by VisiGen, Oxford Nanopore Technologies Ltd., and Pacific Biosciences, respectively.

In pyrosequencing (Voelkerding et al., *Clinical Chem.*, 55: 641-658, 2009; MacLean et al., *Nature Rev. Microbiol.*, 7: 287-296; U.S. Pat. No. 6,210,891; U.S. Pat. No. 6,258,568; each herein incorporated by reference in its entirety), template DNA is fragmented, end-repaired, ligated to adaptors, and clonally amplified in-situ by capturing single template molecules with beads bearing oligonucleotides complementary to the adaptors. Each bead bearing a single template type is compartmentalized into a water-in-oil microvesicle, and the template is clonally amplified using a technique referred to as emulsion PCR. The emulsion is disrupted after amplification and beads are deposited into individual wells of a picotitre plate functioning as a flow cell during the sequencing reactions. Ordered, iterative introduction of each of the four dNTP reagents occurs in the flow cell in the presence of sequencing enzymes and luminescent reporter such as luciferase. In the event that an appropriate dNTP is added to the 3' end of the sequencing primer, the resulting production of ATP causes a burst of luminescence within the well, which is recorded using a CCD camera. It is possible to achieve read lengths greater than or equal to 400 bases, and $1 \times 10^6$ sequence reads can be achieved, resulting in up to 500 million base pairs (Mb) of sequence.

In the Solexa/Illumina platform (Voelkerding et al., *Clinical Chem.*, 55: 641-658, 2009; MacLean et al., *Nature Rev. Microbiol.*, 7: 287-296; U.S. Pat. No. 6,833,246; U.S. Pat. No. 7,115,400; U.S. Pat. No. 6,969,488; each herein incorporated by reference in its entirety), sequencing data are produced in the form of shorter-length reads. In this method, single-stranded fragmented DNA is end-repaired to generate 5'-phosphorylated blunt ends, followed by Klenow-mediated addition of a single A base to the 3' end of the fragments. A-addition facilitates addition of T-overhang adaptor oligonucleotides, which are subsequently used to capture the template-adaptor molecules on the surface of a flow cell that is studded with oligonucleotide anchors. The anchor is used as a PCR primer, but because of the length of the template and its proximity to other nearby anchor oligonucleotides, extension by PCR results in the "arching over" of the molecule to hybridize with an adjacent anchor oligonucleotide to form a bridge structure on the surface of the flow cell. These loops of DNA are denatured and cleaved. Forward strands are then sequenced with reversible dye terminators. The sequence of incorporated nucleotides is determined by detection of post-incorporation fluorescence, with each fluor and block removed prior to the next cycle of dNTP addition. Sequence read length ranges from 36 nucleotides to over 50 nucleotides, with overall output exceeding 1 billion nucleotide pairs per analytical run.

Sequencing nucleic acid molecules using SOLiD technology (Voelkerding et al., *Clinical Chem.*, 55: 641-658, 2009; MacLean et al., *Nature Rev. Microbiol.*, 7: 287-296; U.S. Pat. No. 5,912,148; U.S. Pat. No. 6,130,073; each herein incorporated by reference in their entirety) also involves fragmentation of the template, ligation to oligonucleotide adaptors, attachment to beads, and clonal amplification by emulsion PCR. Following this, beads bearing template are immobilized on a derivatized surface of a glass flow-cell, and a primer complementary to the adaptor oligonucleotide is annealed. However, rather than utilizing this primer for 3' extension, it is instead used to provide a 5' phosphate group for ligation to interrogation probes containing two probe-specific bases followed by 6 degenerate bases and one of four fluorescent labels. In the SOLiD system, interrogation probes have 16 possible combinations of the two bases at the 3' end of each probe, and one of four fluors at the 5' end. Fluor color and thus identity of each probe corresponds to specified color-space coding schemes. Multiple rounds (usually 7) of probe annealing, ligation, and fluor detection are followed by denaturation, and then a second round of sequencing using a primer that is offset by one base relative to the initial primer. In this manner, the template sequence can be computationally reconstructed, and template bases are interrogated twice, resulting in increased accuracy. Sequence read length averages 35 nucleotides, and overall output exceeds 4 billion bases per sequencing run.

In certain embodiments, nanopore sequencing in employed (see, e.g., Astier et al., J Am Chem Soc. 2006 Feb. 8; 128(5):1705-10, herein incorporated by reference). The theory behind nanopore sequencing has to do with what occurs when the nanopore is immersed in a conducting fluid and a potential (voltage) is applied across it: under these conditions a slight electric current due to conduction of ions through the nanopore can be observed, and the amount of current is exceedingly sensitive to the size of the nanopore. If DNA molecules pass (or part of the DNA molecule passes) through the nanopore, this can create a change in the magnitude of the current through the nanopore, thereby allowing the sequences of the DNA molecule to be determined.

HeliScope by Helicos BioSciences (Voelkerding et al., *Clinical Chem.*, 55: 641-658, 2009; MacLean et al., *Nature Rev. Microbiol.*, 7: 287-296; U.S. Pat. No. 7,169,560; U.S. Pat. No. 7,282,337; U.S. Pat. No. 7,482,120; U.S. Pat. No. 7,501,245; U.S. Pat. No. 6,818,395; U.S. Pat. No. 6,911,345; U.S. Pat. No. 7,501,245; each herein incorporated by reference in their entirety) is the first commercialized single-molecule sequencing platform. This method does not require clonal amplification. Template DNA is fragmented and polyadenylated at the 3' end, with the final adenosine bearing a fluorescent label. Denatured polyadenylated template fragments are ligated to poly(dT) oligonucleotides on the surface of a flow cell. Initial physical locations of captured template molecules are recorded by a CCD camera, and then label is cleaved and washed away. Sequencing is achieved by addition of polymerase and serial addition of fluorescently-labeled dNTP reagents. Incorporation events result in fluor signal corresponding to the dNTP, and signal is captured by a CCD camera before each round of dNTP addition. Sequence read length ranges from 25-50 nucleotides, with overall output exceeding 1 billion nucleotide pairs per analytical run.

Another exemplary nucleic acid sequencing approach developed by Stratos Genomics, Inc. that is also optionally adapted for use with the present invention involves the use of Xpandomers. This sequencing process typically includes providing a daughter strand produced by a template-directed synthesis. The daughter strand generally includes a plurality of subunits coupled in a sequence corresponding to a contiguous nucleotide sequence of all or a portion of a target nucleic acid in which the individual subunits comprise a tether, at least one probe or nucleobase residue, and at least one selectively cleavable bond. The selectively cleavable bond(s) is/are cleaved to yield an Xpandomer of a length longer than the plurality of the subunits of the daughter strand. The Xpandomer typically includes the tethers and reporter elements for parsing genetic information in a sequence corresponding to the contiguous nucleotide sequence of all or a portion of the target nucleic acid. Reporter elements of the Xpandomer are then detected. Additional details relating to Xpandomer-based approaches are described in, for example, U.S. Patent Publication No. 20090035777, entitled "HIGH THROUGHPUT NUCLEIC ACID SEQUENCING BY EXPANSION," that was filed Jun. 19, 2008, which is incorporated herein in its entirety.

Other emerging single molecule sequencing methods include real-time sequencing by synthesis using a VisiGen platform (Voelkerding et al., *Clinical Chem.*, 55: 641-658, 2009; U.S. Pat. No. 7,329,492; U.S. patent application Ser. No. 11/671,956; U.S. patent application Ser. No. 11/781,166; each herein incorporated by reference in their entirety) in which immobilized, primed DNA template is subjected to strand extension using a fluorescently-modified polymerase and florescent acceptor molecules, resulting in detectable fluorescence resonance energy transfer (FRET) upon nucleotide addition.

Another real-time single molecule sequencing system developed by Pacific Biosciences (Voelkerding et al., *Clinical Chem.*, 55: 641-658, 2009; MacLean et al., *Nature Rev. Microbiol.*, 7: 287-296; U.S. Pat. No. 7,170,050; U.S. Pat. No. 7,302,146; U.S. Pat. No. 7,313,308; U.S. Pat. No. 7,476,503; all of which are herein incorporated by reference) utilizes reaction wells 50-100 nm in diameter and encompassing a reaction volume of approximately 20 zeptoliters ($10 \times 10^{-21}$ L). Sequencing reactions are performed using immobilized template, modified phi29 DNA polymerase, and high local concentrations of fluorescently labeled dNTPs. High local concentrations and continuous reaction conditions allow incorporation events to be captured in real time by fluor signal detection using laser excitation, an optical waveguide, and a CCD camera.

In certain embodiments, the single molecule real time (SMRT) DNA sequencing methods using zero-mode waveguides (ZMWs) developed by Pacific Biosciences, or similar methods, are employed. With this technology, DNA sequencing is performed on SMRT chips, each containing thousands of zero-mode waveguides (ZMWs). A ZMW is a hole, tens of nanometers in diameter, fabricated in a 100 nm metal film deposited on a silicon dioxide substrate. Each ZMW becomes a nanophotonic visualization chamber providing a detection volume of just 20 zeptoliters ($10^{-21}$ liters). At this volume, the activity of a single molecule can be detected amongst a background of thousands of labeled nucleotides.

The ZMW provides a window for watching DNA polymerase as it performs sequencing by synthesis. Within each chamber, a single DNA polymerase molecule is attached to the bottom surface such that it permanently resides within the detection volume. Phospholinked nucleotides, each type labeled with a different colored fluorophore, are then introduced into the reaction solution at high concentrations which promote enzyme speed, accuracy, and processivity. Due to the small size of the ZMW, even at these high, biologically relevant concentrations, the detection volume is occupied by nucleotides only a small fraction of the time. In addition, visits to the detection volume are fast, lasting only a few microseconds, due to the very small distance that diffusion has to carry the nucleotides. The result is a very low background.

Processes and systems for such real time sequencing that may be adapted for use with the invention are described in, for example, U.S. Pat. No. 7,405,281, entitled "Fluorescent nucleotide analogs and uses therefor", issued Jul. 29, 2008 to Xu et al., U.S. Pat. No. 7,315,019, entitled "Arrays of optical confinements and uses thereof", issued Jan. 1, 2008 to Turner et al., U.S. Pat. No. 7,313,308, entitled "Optical analysis of molecules", issued Dec. 25, 2007 to Turner et al., U.S. Pat. No. 7,302,146, entitled "Apparatus and method for analysis of molecules", issued Nov. 27, 2007 to Turner et al., and U.S. Pat. No. 7,170,050, entitled "Apparatus and methods for optical analysis of molecules", issued Jan. 30, 2007 to Turner et al., U.S. Patent Publications Nos. 20080212960, entitled "Methods and systems for simultaneous real-time monitoring of optical signals from multiple sources", filed Oct. 26, 2007 by Lundquist et al., 20080206764, entitled "Flowcell system for single molecule detection", filed Oct. 26, 2007 by Williams et al., 20080199932, entitled "Active surface coupled polymerases", filed Oct. 26, 2007 by Hanzel et al., 20080199874, entitled "CONTROLLABLE STRAND SCISSION OF MINI CIRCLE DNA", filed Feb. 11, 2008 by Otto et al., 20080176769, entitled "Articles having localized molecules disposed thereon and methods of producing same", filed Oct. 26, 2007 by Rank et al., 20080176316, entitled "Mitigation of photodamage in analytical reactions", filed Oct. 31, 2007 by Eid et al., 20080176241, entitled "Mitigation of photodamage in analytical reactions", filed Oct. 31, 2007 by Eid et al., 20080165346, entitled "Methods and systems for simultaneous real-time monitoring of optical signals from multiple sources", filed Oct. 26, 2007 by Lundquist et al., 20080160531, entitled "Uniform surfaces for hybrid material substrates and methods for making and using same", filed Oct. 31, 2007 by Korlach, 20080157005, entitled "Methods and systems for simultaneous real-time monitoring of optical signals from multiple sources", filed Oct. 26, 2007 by Lundquist et al., 20080153100, entitled "Articles having localized molecules disposed thereon and methods of producing same", filed Oct. 31, 2007 by Rank et al., 20080153095, entitled "CHARGE SWITCH NUCLEOTIDES", filed Oct. 26, 2007 by Williams et al., 20080152281, entitled "Substrates, systems and methods for analyzing materials", filed Oct. 31, 2007 by Lundquist et al., 20080152280, entitled "Substrates, systems and methods for analyzing materials", filed Oct. 31, 2007 by Lundquist et al., 20080145278, entitled "Uniform surfaces for hybrid material substrates and methods for making and using same", filed Oct. 31, 2007 by Korlach, 20080128627, entitled "SUBSTRATES, SYSTEMS AND METHODS FOR ANALYZING MATERIALS", filed Aug. 31, 2007 by Lundquist et al., 20080108082, entitled "Polymerase enzymes and reagents for enhanced nucleic acid sequencing", filed Oct. 22, 2007 by Rank et al., 20080095488, entitled "SUBSTRATES FOR PERFORMING ANALYTICAL REACTIONS", filed Jun. 11, 2007 by Foquet et al., 20080080059, entitled "MODULAR OPTICAL COMPONENTS AND SYSTEMS INCORPORATING SAME", filed Sep. 27, 2007 by Dixon et al., 20080050747, entitled "Articles having localized molecules disposed thereon and methods of producing and using same", filed Aug. 14, 2007 by Korlach et al., 20080032301, entitled "Articles having localized molecules disposed thereon and methods of producing same", filed Mar. 29, 2007 by Rank et al., 20080030628, entitled "Methods and systems for simultaneous real-time monitoring of optical signals from multiple sources", filed Feb. 9, 2007 by Lundquist et al., 20080009007, entitled "CONTROLLED INITIATION OF PRIMER EXTENSION", filed Jun. 15, 2007 by Lyle et al., 20070238679, entitled "Articles having localized molecules disposed thereon and methods of producing same", filed Mar. 30, 2006 by Rank et al., 20070231804, entitled "Methods, systems and compositions for monitoring enzyme activity and applications thereof", filed Mar. 31, 2006 by Korlach et al., 20070206187, entitled "Methods and systems for simultaneous real-time monitoring of optical signals from multiple sources", filed Feb. 9, 2007 by Lundquist et al., 20070196846, entitled "Polymerases for nucleotide analogue incorporation", filed Dec. 21, 2006 by Hanzel et al., 20070188750, entitled "Methods and systems for simultaneous real-time monitoring of optical signals from multiple sources", filed Jul. 7, 2006 by Lundquist et al., 20070161017, entitled "MITIGATION OF PHOTODAMAGE IN ANALYTICAL REACTIONS", filed Dec. 1, 2006 by Eid et al., 20070141598, entitled "Nucleotide Compositions and Uses Thereof", filed Nov. 3, 2006 by Turner et al., 20070134128, entitled "Uniform surfaces for hybrid material substrate and methods for making and using same", filed Nov. 27, 2006 by Korlach, 20070128133, entitled "Mitigation of photodamage in analytical reactions", filed Dec. 2, 2005 by Eid et al., 20070077564, entitled "Reactive surfaces, substrates and methods of producing same", filed Sep. 30, 2005 by Roitman et al., 20070072196, entitled "Fluorescent nucleotide analogs and uses therefore", filed Sep. 29, 2005 by Xu et al., and 20070036511, entitled "Methods and systems for monitoring multiple optical signals from a single source", filed Aug. 11, 2005 by Lundquist et al., and Korlach et al. (2008) "Selective aluminum passivation for targeted immobilization of single DNA polymerase molecules in zero-mode waveguide nanostructures" Proc. Nat'l. Acad. Sci. U.S.A. 105(4): 11761181—all of which are herein incorporated by reference in their entireties.

EXAMPLES

Example 1

Single-Tube DNA Library Generation

This Example describes an exemplary single-tube method for generating DNA libraries from small amount of starting material that does not require DNA purification between steps and which employs a universal buffer. The method is generally outlined in FIG. 1. Briefly, the process starts with an aqueous samples which is then subjected to a lysis/nucleic acid extraction protocol and eluted in a universal whole genome amplification (WGA) buffer. The composition of the buffer is shown in Table 1:

TABLE 1

| Tris Ph 7.5 | 50.00 mM |
|---|---|
| MgCl2 | 9.00 mM |
| (NH4)2SO4 | 7.50 mM |
| Sonicated Poly Adenylic acid | 1.00 Ng/ul |
| Trehalose | 0.60 M |
| DNTP mix | 100 mM (25 mM each) |
| Bioline | 2.00 mM |
| DTT | 4.00 mM |
| Primers | 50.00 uM |
| BSA | 0.23 ug/ul |
| Tween-40 | 1.00% |

The sample is then heated at 95 C. for 1 minute to denature the genomic DNA and allow the short random primers to bind. After cooling to an appropriate temperature (e.g., ~37 C.) the WGA enzyme mix is added, which includes phi 29 polymerase, klenow exo-polymerase, polynucleotide kinase and pyrophosphatase, and incubated for 30 minutes at 37 C. to amplify the genomic material.

The sample is then physically sheared (e.g., by sonication) and allowed to incubate another 30 minutes at 30 C. to polish the ends of the now sheared molecules. After incubation at an elevated temperature to inactivate the polymerase (e.g., 75 C. for 10 minutes) DNA linkers are added (in this Example, hairpin oligos as described below) as well as T4 ligase and ATP. The reaction is allowed to incubate at 25 C. for an appropriate amount of time (blunt ends are done in ~15 minutes, A-tailed end reactions take longer.) In this Example, single stranded circular DNA molecules are generated. As such, exonucleases are then added to remove any non circularized DNA present with an incubation at 37 C. It is noted that if this Example were creating non-circularized templates for different sequencing technologies, one could change exonucleases and include some 5' and/or 3' blocking agents on the adapters to achieve the same result. The exonucleases are then heat inactivated at 95 C and the sample treated with further clean up reagents, including Pro-K to remove enzyme/ protein components and a phosphatase to remove unused dNTPs (although other clean up procedures such as those with resin could also be used.) After an appropriate incubation time and temperature and elevated temperature to inactivate the clean up enzymes the reactions proceeds through a final clean up/size selection process (e.g., such as bind-elute and flow through resins).

Figure 2:
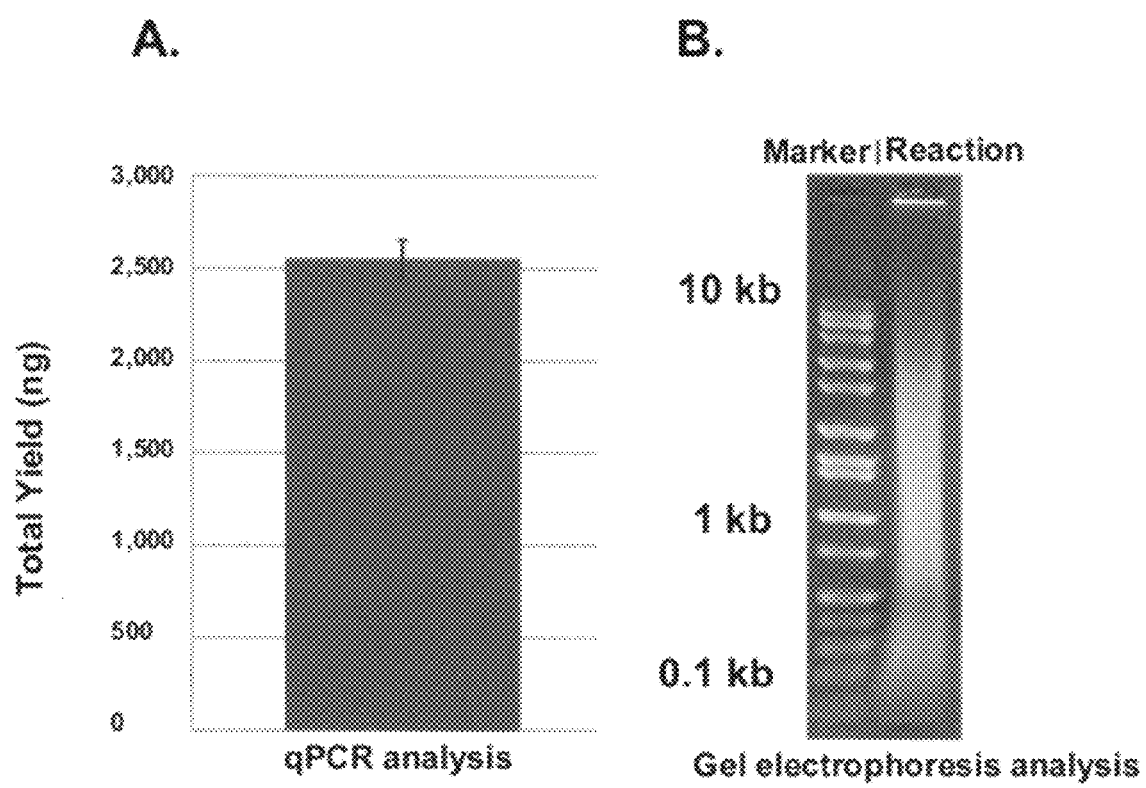
FIG. 2 shows results from Example 1 and shows the ability to amplify ng levels of DNA to ug levels in 30 minutes using phi 29/klenow exo-polymerases in whole genome amplification (WGA).

FIG. 2 shows the yield that can be obtained with WGA starting with 1 ng of *Klebsiella pneumoniae* (Kp) genomic DNA using the methods described above. By Kp specific DNA the yield is over 2.5 ug (2500× fold amplification) with gel electrophoresis showing the typical smear pattern seen with WGA reactions and an appropriate amount of total DNA.

The materials and methods used for generating the data in FIG. 2 are as follows. One (1) ng *K. pneumoniae* (Kp) purified genomic DNA serves as starting material. The buffer in Table 1, 100 units Phi 29, and 40 units Klenow exo- are employed for WGA using the following reaction conditions: 100 ul total volume, heat to 95 C. for 1 m prior to enzyme addition, cool samples to 4 C., then after adding enzyme and mixing, 37 C. for 30 min, then 75 C. for 10 min. FIG. 2A shows total yield of amplified product as measured by qPCR, and FIG. 2B shows a gel electrophoresis analysis of amplified product using 1% agarose, ethidium bromide UV light visualization.

Figure 3:
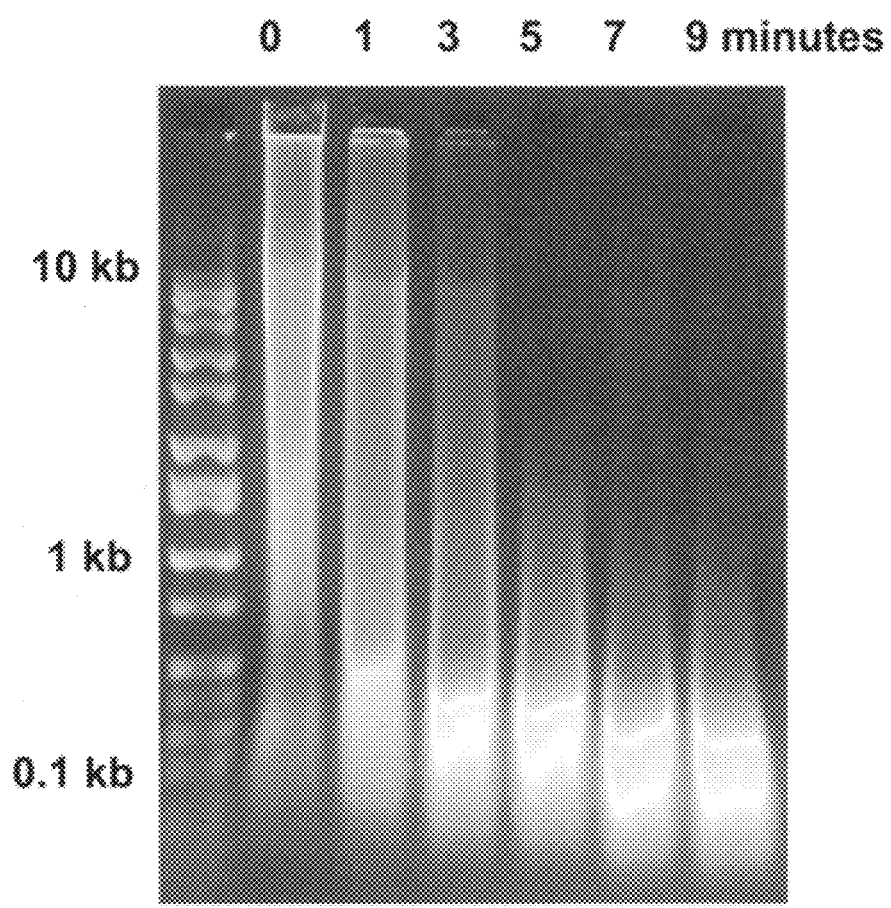
FIG. 3 shows results from Example 1 and shows the ability of sonication to fragment the WGA DNA in WGA buffer to lengths in the 100s of base pairs.

Whole genome DNA (20 ul) as prepared in FIG. 2 was sonicated in a thin wall PCR tube floating in a 4 C. water bath using a cup horn sonicator (Misonix 3000, power level 10 (full power ~200 w)) for the appropriate amount of time. 10 ul aliquots of these reactions were then run on 1% EtBr/agarose gel for 45 minutes at 100V and a UV light source. FIG. 3 shows the effect of different amounts of sonication time on the size of WGA DNA in A9 buffer. After 5 minutes most of the DNA is in the 100's of by range which is a reasonable range for a number of sequencing technologies (although if smaller pieces are needed further sonication can reduce the size further.)

Next, "before rxn" oligos (shown below, final concentration of 1 μM each) were hybridized to each other and mixed with buffer in Table 1 and 100 units phi 29 and 40 units klenow exo-. This reaction was then incubated for 30 min at 30 C. followed by 75 C. for 10 minutes. The sample was then analyzed by ESI-TOF mass spectrometry using the T5000 system both before (FIG. 4A) and after (FIG. 4B) addition of WGA enzymes. The sequences of end polished oligos are shown below with an addition untemplated A (majority product)

Before Rxn

```
Top strand:
                                       (SEQ ID NO: 1)
CATGCGGATGCAGAGGAGGACGACTCTGATGTCT Bottom strand:
                                       (SEQ ID NO: 2)
GCAATGAAGACATCAGAGTCGTCCTCCTCTGCATCCGCATGTGT
```

After Rxn (with +A Shown)

```
Top strand:
                                       (SEQ ID NO: 3)
CATGCGGATGCAGAGGAGGACGACTCTGATGTCTTCATTGCA Bottom strand:
                                       (SEQ ID NO: 4)
GCAATGAAGACATCAGAGTCGTCCTCCTCTGCATCCGCATGA
```

Figure 4:
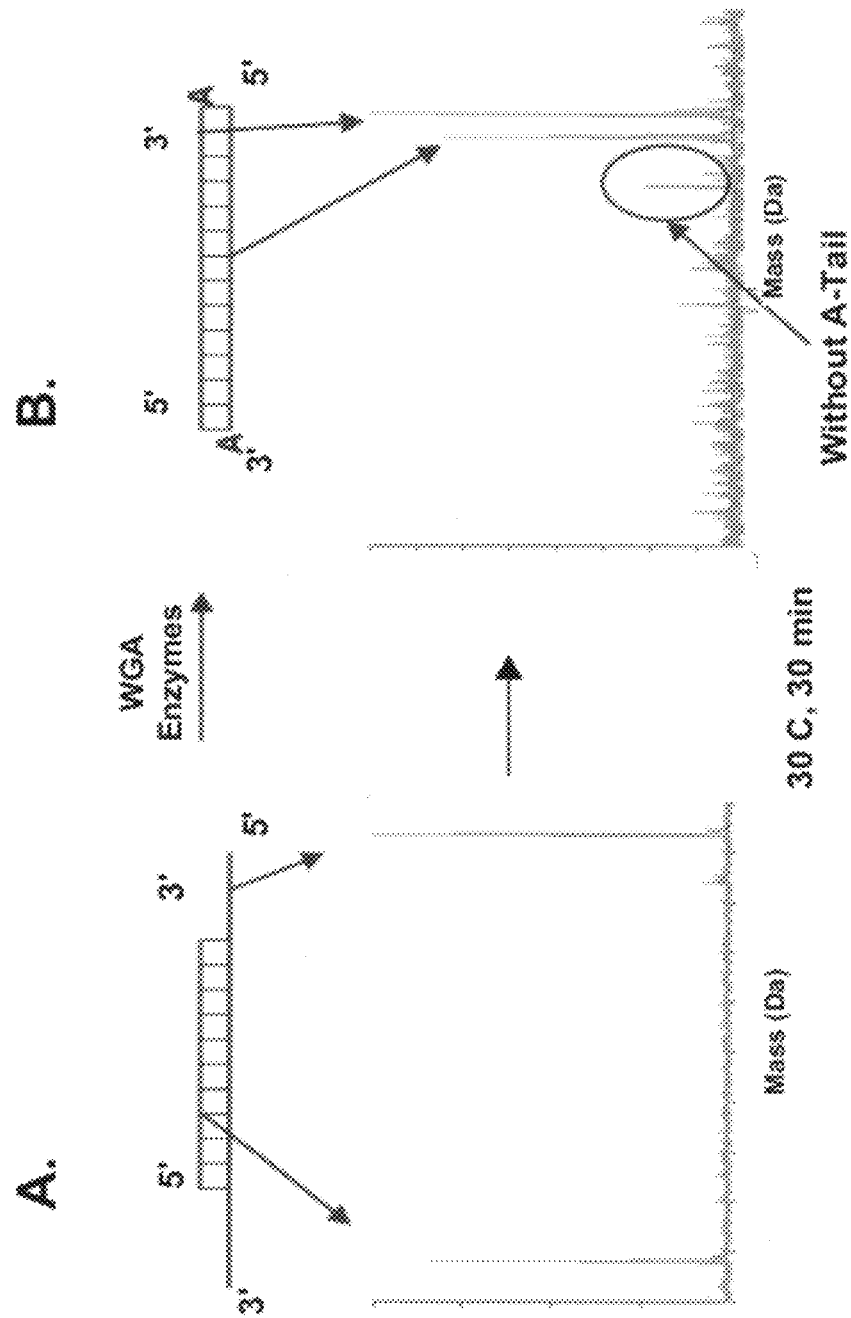
FIG. 4 shows results from Example 1 and shows the ability of phi 29/klenow exo-enzyme mix in WGA buffer to blunt and a-tail DNA using DNA oligos and mass spectrometry for analysis. Results of sample analysis by ESI-TOF mass spectrometry using the T5000 system show both before (FIG. 4A) and after (FIG. 4B) addition of WGA enzymes.

In FIG. 4 it is shown that the enzymes used for WGA in the A9 buffer will end polish and A-tail DNA oligos used to model sheared DNA when incubated at 30 C. for 30 minutes. In this portion of the Example, a set of oligos was used that when hybridized have both a 5' and 3' overhang allowing for the WGA enzymes to chew back the 3' overhang and fill in opposite the 5' overhang giving blunt end DNA molecules which can then have an untemplated A-added. After the incubation at 30 C. for 30 min, the samples were heated at 75 C. for 10 minutes and analyzed using an ESI-TOF mass spectrometry (T5000 system.)

Next, "before rxn" oligos (shown below, final concentration of 1 μM each) were hybridized to each other and mixed with buffer in Table 1 above and 100 units phi 29 and 40 units klenow exo-. This reaction was then incubated for 5 min at 37 C. followed by 75 C. for 10 minutes. The sample was then analyzed by ESI-TOF mass spectrometry using the T5000 system showing sample analysis both before (FIG. 5A) and after (FIG. 5B) the addition of WGA enzymes. The sequences of end polished oligos depicted in the right portion of the figure are shown below with blunt ends (majority product). Before Rxn

```
    Top strand:
                                     (SEQ ID NO: 1)
    CATGCGGATGCAGAGGAGGACGACTCTGATGTCT Bottom strand:
                                     (SEQ ID NO: 2)
    GCAATGAAGACATCAGAGTCGTCCTCCTCTGCATCCGCATGTGT
```

After Rxn (with +A Shown)

```
    Top strand:
                                     (SEQ ID NO: 5)
    CATGCGGATGCAGAGGAGGACGACTCTGATGTCTTCATTGC Bottom strand:
                                     (SEQ ID NO: 6)
    GCAATGAAGACATCAGAGTCGTCCTCCTCTGCATCCGCATG
```

Figure 5:
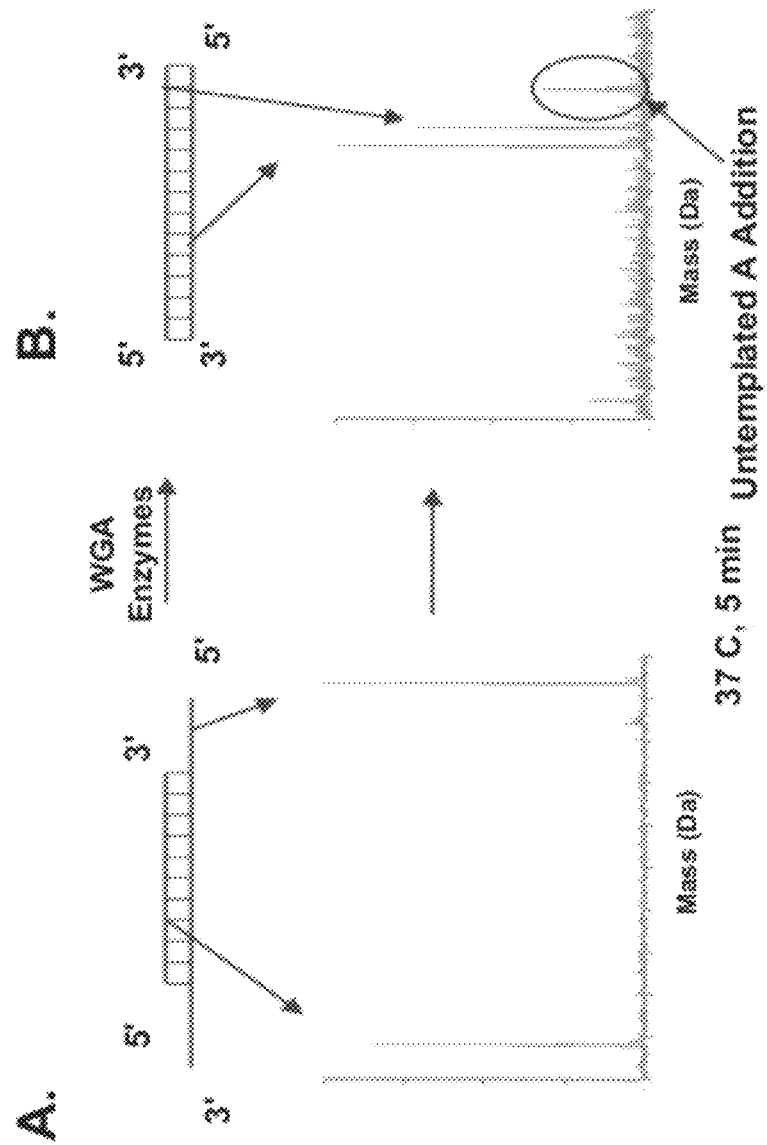
FIG. 5 shows results from Example 1 and shows the ability of phi 29/klenow exo-enzyme mix in WGA buffer to blunt end DNA using DNA oligos and mass spectrometry for analysis. Results of sample analysis by ESI-TOF mass spectrometry using the T5000 system show sample analysis both before (FIG. 5A) and after (FIG. 5B) the addition of WGA enzymes.

In FIG. 5, its shown that the enzymes used for WGA in the buffer from Table 1 will end polish but not A-tail DNA oligos used to model sheared DNA when incubated at 37 C. for 5 minutes. Specifically, when the above set of oligos were used which, when hybridized, have both a 5' and 3' overhang allowing for the WGA enzymes to chew back the 3' overhang and fill in opposite the 5' overhang giving blunt end DNA molecules. After the incubation at 37 C. for 5 min, the samples were heated at 75 C. for 10 minutes and analyzed using an ESI-TOF mass spectrometry (T5000 system.)

Next, two complementary oligos were hybridized to each other giving a blunt end duplex with no 5' or 3' phosphates. This duplex was mixed with the buffer from Table 1 and 5 units polynucleotide kinase and incubated for 30 minutes at 30 C. followed by 75 C. for 10 min. The sample was then analyzed by ESI-TOF mass spectrometry using the T5000 system.

```
                                     (SEQ ID NO: 7)
    Oligo#1 5'  TGCGGATGCAGAGGAGGATGACTCTGATGTCT (SEQ ID NO: 8)
    Oligo#2 5'  AGACATCAGAGTCATCCTCCTCTGCATCCGCA
```

Figure 6:
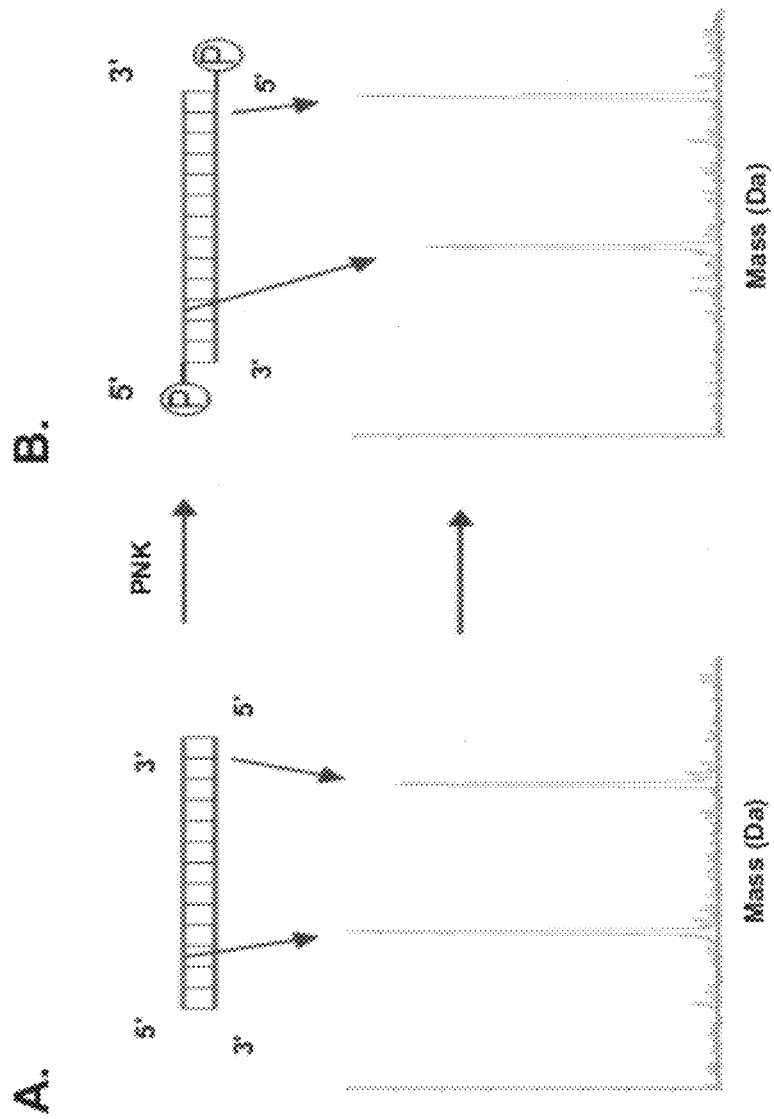
FIG. 6 shows results from Example 1 and shows the ability of poly nucleotide kinase in WGA buffer to phosphorylate the 5' ends of DNA using DNA oligos and mass spectrometry for analysis.

In FIG. 6 shows that polynucleotide kinase will phosphorylate DNA in the buffer from Table 1. Specifically, the above set of oligos, which when hybridized, have blunt ends and no 5' phosphate were employed. After incubation with polynucleotide kinase at 37 C. for 30 minutes, the reactions were heated to 75 C. for 10 min and analyzed using ESI-TOF mass spectrometry (T5000 system.). FIG. 6 shows analysis of the sample with the oligos before (FIG. 6A) and after (FIG. 6B) addition of polynucleotide kinase.

Next, two complementary oligos each with a 5' overhang were hybridized together. A hairpin oligo with a complementary 5' overhang was also hybridized separately. These oligos were then mixed in the buffer from Table 1 with 1000 cohesive end ligation units of T4 DNA ligase. This reaction was then incubated for the appropriate amount of time (30, 60, 120 min) at 16 C. followed by 75 C. for 10 minutes. The samples (including controls of only hairpin, only insert and hairpin+insert but with no ligase) were then run on a 1% agarose gel and visualized using ethidium bromide and a uv light source. Insert Oligos:

```
                                     (SEQ ID NO: 9)
    5'-P-GAAGCATGCGGATGCAGAGGAGGACGACTCTGATGTCTTCATTGC (SEQ ID NO: 10)
    5'-P-GAAGGCAATGAAGACATCAGAGTCGTCCTCCTCTGCATCCGCATG
```

Hairpin Oligo

```
                                     (SEQ ID NO: 11)
    5'-P-CTTCTCTCTCTcttttcctcctcctccgttgttgttgttGAGAG

AGA
```

Figure 7:
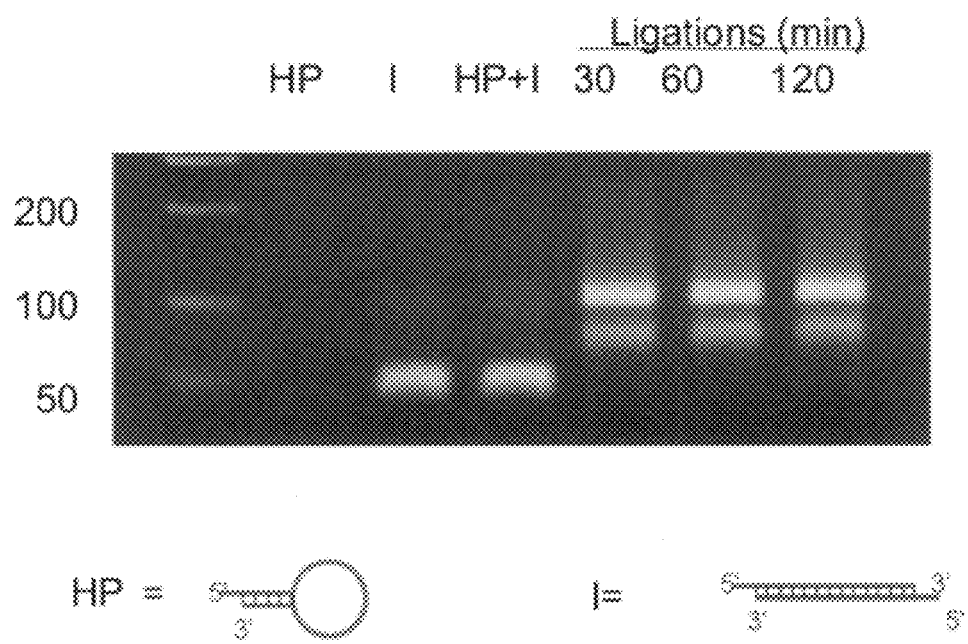
FIG. 7 shows results from Example 1 and shows the ability to ligate DNA fragments using T4 ligase in WGA buffer using DNA oligos and gel electrophoresis analysis.

Complementary 5' overhangs are in bold, complementary stem of hairpin structure is underlined, lowercase bases of hairpin indicate unpaired bases FIG. 7 shows that by gel electrophoresis, one can perform ligation reactions in the buffer in Table 1 using T4 DNA ligase and ATP. Specifically, the above set of oligos which, when hybridized, have a 5' "sticky end" on both ends of the duplex DNA molecule and a hairpin oligo which has a complementary 5' "sticky end" overhang. Ligations were performed at 16 C. in the buffer in Table 1 with ATP added. For analysis, gel electrophoresis was used and it showed that after 30 minutes the reaction was complete giving mostly a product that migrates at ~120 bp, a minor product which migrates at ~75 bp and no "insert" starting material (which migrates at ~50 bp.) (Note: the hairpin oligo is not visible on the gel despite its high concentration due to the significant single stranded portion of the oligo which allow for minimal intercalation by ethidium bromide.)

Next, the same two complementary oligos each with a 5' overhang were hybridized together (SEQs 9 and 10). A hairpin oligo with a complementary 5' overhang was also hybridized separately (SEQ ID NO:11). These oligos were then mixed in the buffer in Table 1 with 1000 cohesive end ligation units of T4 DNA ligase. This reaction was then incubated for the appropriate amount of time 30 minutes at 16 C. followed by 75 C. for 10 minutes. The samples (including a control of hairpin+insert but with no ligase) were then run on an ESI-TOF mass spectrometer using the T5000 system.

Figure 8:
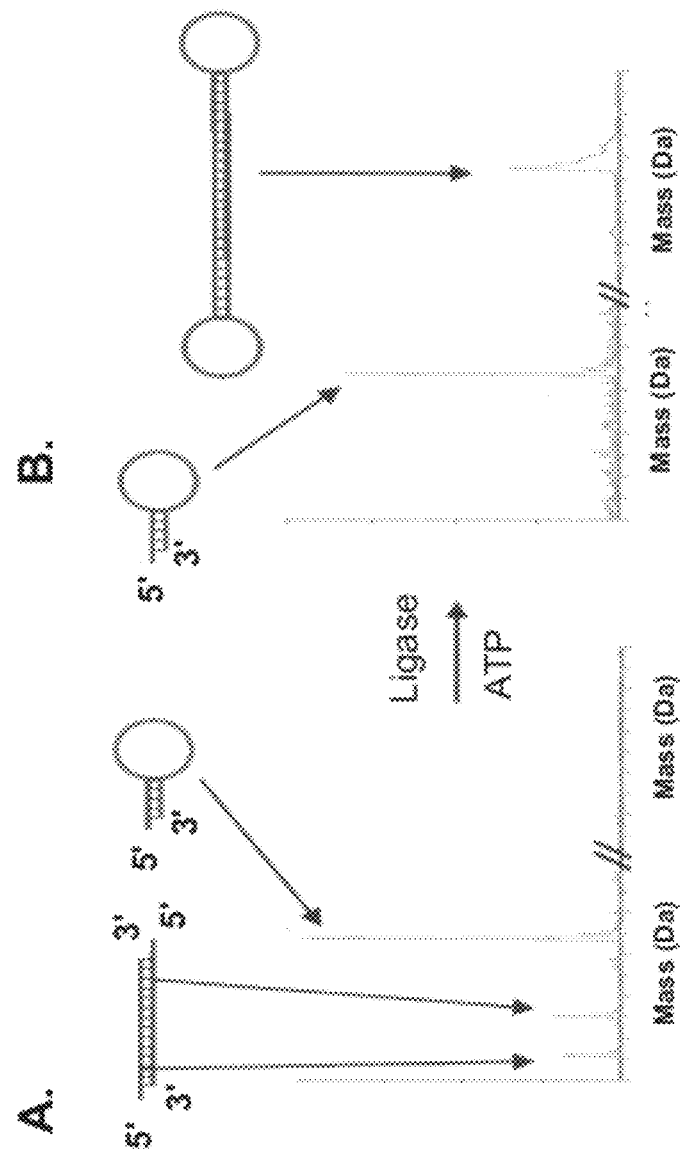
FIG. 8 shows results from Example 1 and shows the ability to ligate DNA fragments using T4 ligase in WGA buffer using DNA oligos and mass spectrometry analysis. Sample analysis with (FIG. 8A) and without ligase (FIG. 8B) was conducted with an ESI-TOF mass spectrometer.

FIG. 8 shows that by mass spectral analysis one can perform ligation reactions in the buffer in Table 1 using T4 DNA ligase and ATP. The set of oligos show above were used which when hybridized have a 5' "sticky end" on both ends of the duplex DNA molecule and a hairpin oligo which has a complementary 5' "sticky end" overhang. Ligations were performed at 16 C. for 30 min in the buffer in Table 1 with ATP added. For analysis, a mixture of hairpin "insert" oligos and "hairpin" oligos with (FIG. 8A) or without the addition of ligase (FIG. 8B) were analyzed using ESI-TOF mass spectrometry. This showed that without ligase, only starting materials were visualized, but with ligase, no insert oligos were visualized and instead the presence of a high molecular weight product which corresponds to an insert duplex molecule with a hairpin oligo ligated on either end (hairpin is still observed in +ligase reaction because it was at 10× the insert starting concentration.)

Next, two complementary oligos each with a 5' overhang were hybridized together (SEQs 9 and 10). A hairpin oligo with a complementary 5' overhang was also hybridized separately (SEQ ID NO:11). These oligos were then mixed in the buffer from Table 1 with 1000 cohesive end ligation units of T4 DNA ligase. This reaction was then incubated for the appropriate amount of time 30 minutes at 16 C. followed by 75 C. for 10 minutes. The reaction was then mixed with exonuclease III and exonuclease VII and incubated for 30 minutes at 37 C. This sample and controls of only insert, only hairpin, and a ligation reaction not treated with the exonucleases was run on a 1% agarose gel and visualized by ethidium bromide and a uv light source.

Figure 9:
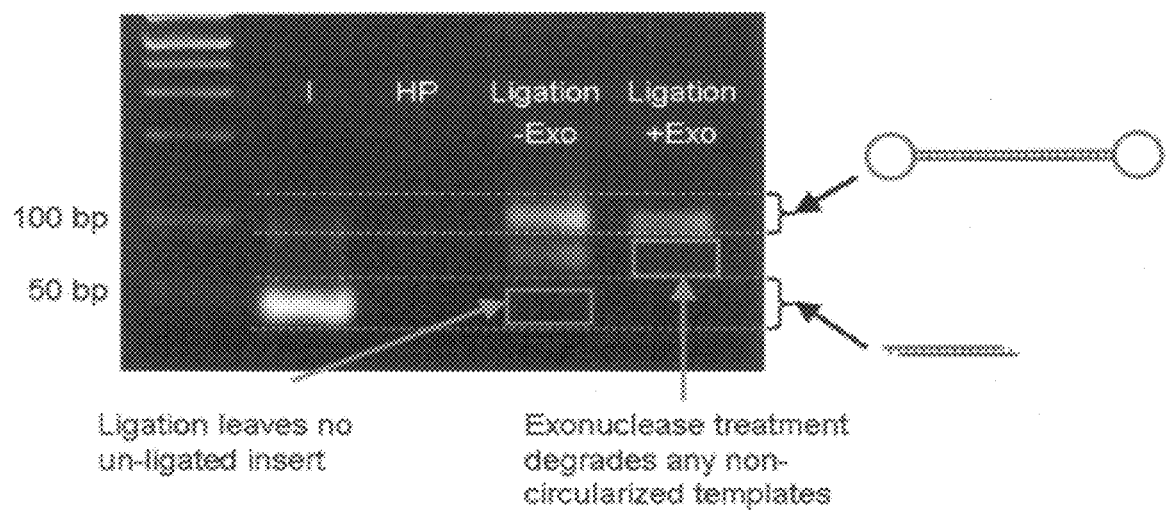
FIG. 9 shows results from Example 1 and shows the ability to exonuclease digest DNA using exonuclease III and exonuclease VII in WGA buffer using DNA oligos and gel electrophoresis analysis.

FIG. 9 shows that exonucleases (specifically Exo II and Exo VII) are functional in the buffer in Table 1 and can be used to remove non-circular DNA products from the reaction. These reactions used ligation reactions as run in FIGS. 8 and 9 and subjected them to exonuclease III and exonuclease VII for 30 minutes at 37 C. The samples were then analyzed using gel electrophoresis showing the removal of non-circular products and the retention of circular products.

Next, the same two complementary oligos each with a 5' overhang were hybridized together (SEQs 9 and 10). A hairpin oligo with a complementary 5' overhang was also hybridized separately (SEQ ID NO:11). These oligos were then mixed in the buffer from Table 1 with 1000 cohesive end ligation units of T4 DNA ligase. This reaction was then incubated for the appropriate amount of time 30 minutes at 16 C. followed by 75 C. for 10 minutes. The reaction was then mixed with exonuclease III and exonuclease VII and incubated for 30 minutes at 37 C. This sample (FIG. 10B) and a ligation reaction not treated with the exonucleases (FIG. 10B) were then run on an ESI-TOF mass spectrometer using the T5000 system.

FIG. 10 shows that exonucleases (specifically Exo II and Exo VII) are functional in the buffer from Table 1 and can be used to remove non-circular DNA products from the reaction. These reactions used ligation reactions as run in FIGS. 8 and 9 and subjected them to exonuclease III and exonuclease VII for 30 minutes at 37 C. The samples were then analyzed using ESI-TOF mass spectrometry showing the removal of non-circular products and the retention of circular products.

All publications and patents mentioned in the present application are herein incorporated by reference. Various modification and variation of the described methods and compositions of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in the relevant fields are intended to be within the scope of the following claims.

We claim:

1. A method of preparing a nucleic acid library in a multi-purpose buffer, comprising:
   a) combining a nucleic acid sample with a multi-purpose buffer, wherein said multi-purpose buffer comprises deoxyribonucleotide triphosphates (dNTPs) and primers to generate a mixture comprising said nucleic acid sample and said multi-purpose buffer;
   b) contacting said mixture comprising said nucleic acid sample and said multi-purpose buffer with a plurality of purified enzymes, wherein said plurality of purified enzymes comprise a first enzyme with polymerase activity, a second enzyme with kinase activity, and a third enzyme with phosphatase activity, and wherein said contacting is under conditions such that amplified nucleic acid is generated in said multipurpose buffer;
   c) mechanically, physically, chemically or enzymatically treating said amplified nucleic acid in said multi-purpose buffer such that sheared amplified nucleic acid is generated in said multi-purpose buffer without purification of said sheared amplified nucleic acid;
   d) treating said multi-purpose buffer comprising said sheared amplified nucleic acid to inactivate said polymerase activity, said kinase activity, and said phosphatase activity without purification of said sheared amplified nucleic acid; and
   e) contacting said multi-purpose buffer comprising said sheared amplified nucleic acid and said inactive polymerase, kinase and phosphatase with a ligase and nucleic acid adapters without purification of said sheared amplified nucleic acid under conditions such that an adapter-linked nucleic acid library is generated.

2. The method of claim 1, wherein said nucleic acid sample comprises genomic DNA, and wherein the amplified nucleic acid is generated by whole genome amplification.

3. The method of claim 1, wherein said steps a)-e) are conducted in a single container.

4. The method of claim 1, further comprising contacting said multi-purpose buffer containing said adapter-linked nucleic acid library with a proteinase and phosphatase, resin or column such that proteins and dNTPs are removed from said multi-purpose buffer.

5. The method of claim 1, wherein said multi-purpose buffer further comprises an emulsifier.

6. The method of claim 1, wherein said multi-purpose buffer further comprises tris(hydroxymethyl)aminomethane (TRIS).

7. The method of claim 1, wherein said multi-purpose buffer further comprises a divalent metal cation.

8. The method of claim 1, wherein said multi-purpose buffer further comprises an inorganic salt.

9. The method of claim 1, wherein said multi-purpose buffer further comprises polyadenylic acid.

10. The method of claim 1, wherein said multi-purpose buffer further comprises an alpha-linked disaccharide.

11. The method of claim 1, wherein said multi-purpose buffer further comprises a reducing agent.

12. The method of claim 1, wherein said multi-purpose buffer further comprises albumin or albumin-like protein.

13. The method of claim 1, wherein said nucleic acid sample is an amount that is between 10 pg and 50 ng.

* * * * *